United States Patent [19]

Macemon et al.

[11] Patent Number: 5,143,084
[45] Date of Patent: Sep. 1, 1992

[54] DISPOSABLE CARTRIDGE FOR SAMPLING AND ANALYZING BODY FLUIDS

[75] Inventors: James H. Macemon, Redmond; Mark S. Schlosser, Seattle, both of Wash.

[73] Assignee: SpaceLabs, Inc., Redmond, Wash.

[21] Appl. No.: 615,747

[22] Filed: Nov. 16, 1990

Related U.S. Application Data

[63] Continuation-in-part of Ser. No. 528,801, May 24, 1990, abandoned.

[51] Int. Cl.⁵ .................................................. A61B 5/00
[52] U.S. Cl. ...................................... 128/771; 128/762
[58] Field of Search ............... 128/760, 762, 763, 766, 128/770, 771; 604/181, 185

[56] References Cited

U.S. PATENT DOCUMENTS

| | | | |
|---|---|---|---|
| 3,776,218 | 12/1973 | Svensson | 128/2 F |
| 3,785,772 | 1/1974 | Coggeshall | 128/760 |
| 3,912,455 | 10/1975 | Lichtenstein | 128/762 |
| 4,077,395 | 3/1978 | Woolner | 128/762 |
| 4,608,996 | 9/1986 | Brown | 128/760 |
| 4,696,309 | 9/1987 | Stephan | 128/762 |
| 4,784,157 | 11/1988 | Halls et al. | 128/762 |
| 4,999,307 | 3/1991 | Oakley | 128/762 |

FOREIGN PATENT DOCUMENTS 1538196 1/1979 United Kingdom .

*Primary Examiner*—Max Hindenburg
*Attorney, Agent, or Firm*—Seed and Berry

[57] ABSTRACT

A disposable sampling cartridge for use with a blood sample analyzer. The cartridge includes a blood reservoir communicating with a hypodermic needle, a waste collection chamber adapted to receive waste fluids from the blood sample analyzer, and a plurality of ampules each containing a respective analyzing fluid adapted for use by the blood sample analyzer. Each of the ampules contain a piston, and the analyzing fluids in the ampules are expelled by forcing an actuating rod through a frangible wall of the ampule to displace the piston. In one embodiment, the analyzing fluids are withdrawn through a conduit in the actuating rod while the blood and spent analyzing fluids flow through the blood reservoir port on which the hypodermic needle is mounted. In another embodiment the waste fluid flows through an inlet port while the analyzing fluids from the ampules flow through a common port outlet port which selectively communicates with the blood reservoir and the ampules by a valve arrangement.

51 Claims, 12 Drawing Sheets

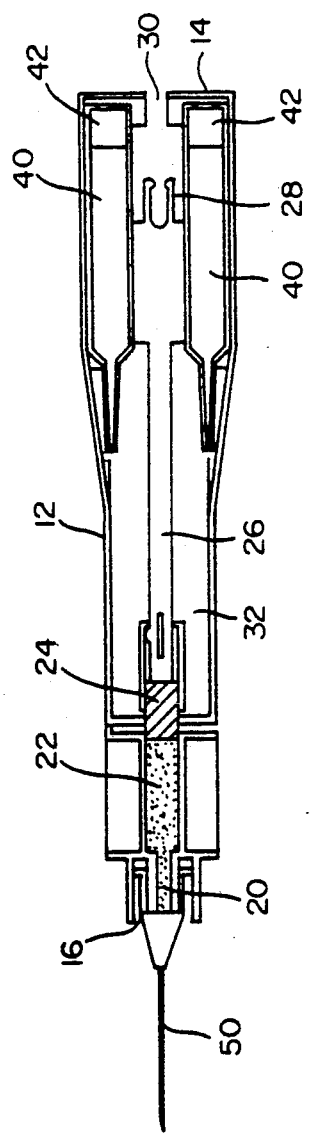
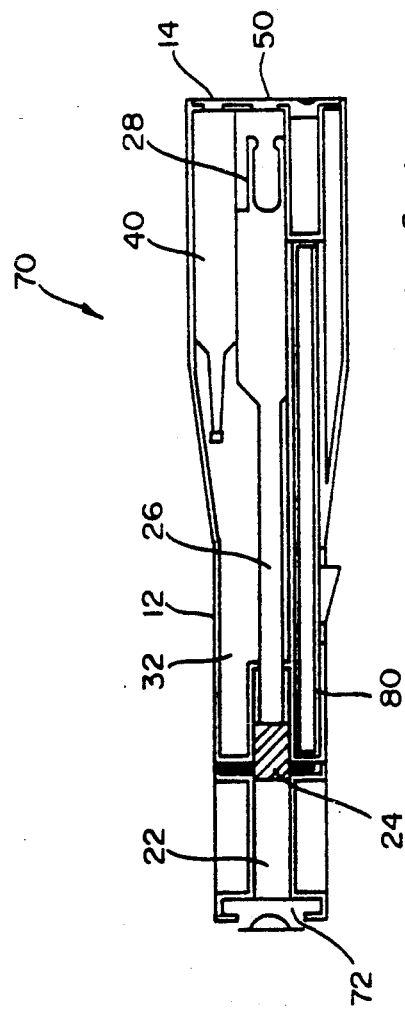
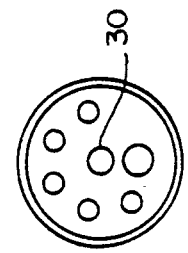
FIG. 2
FIG. 4A
FIG. 4B

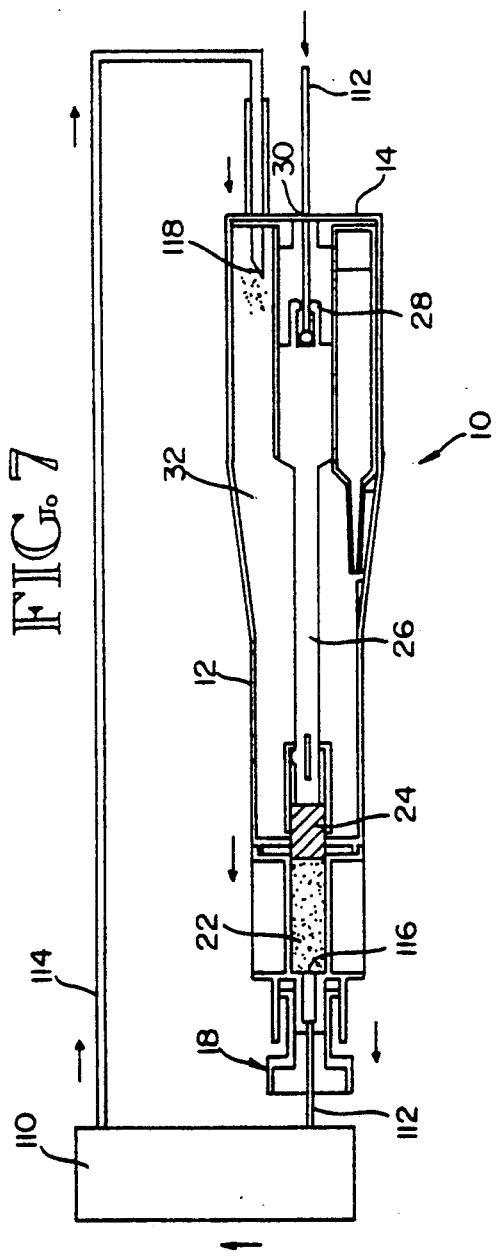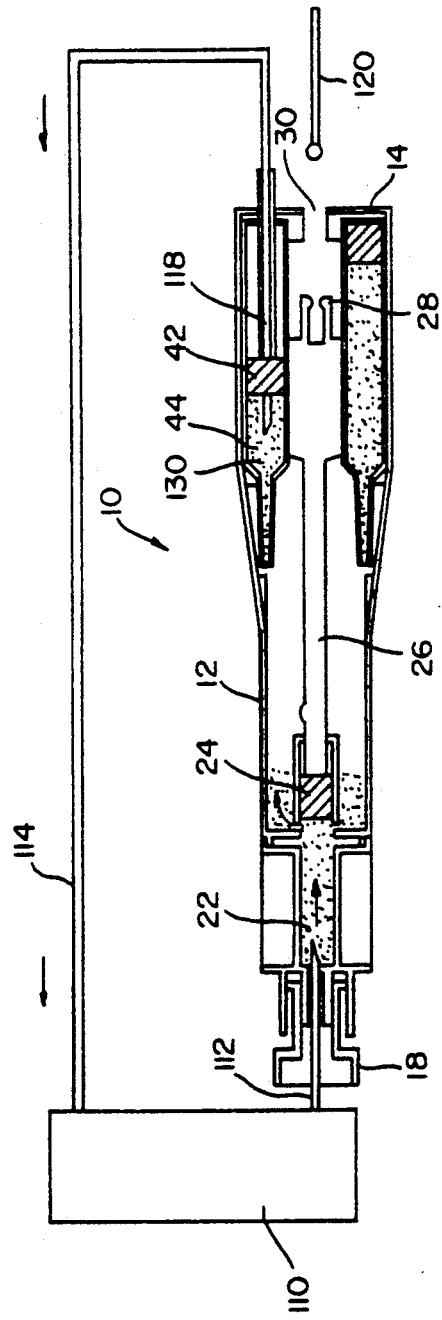

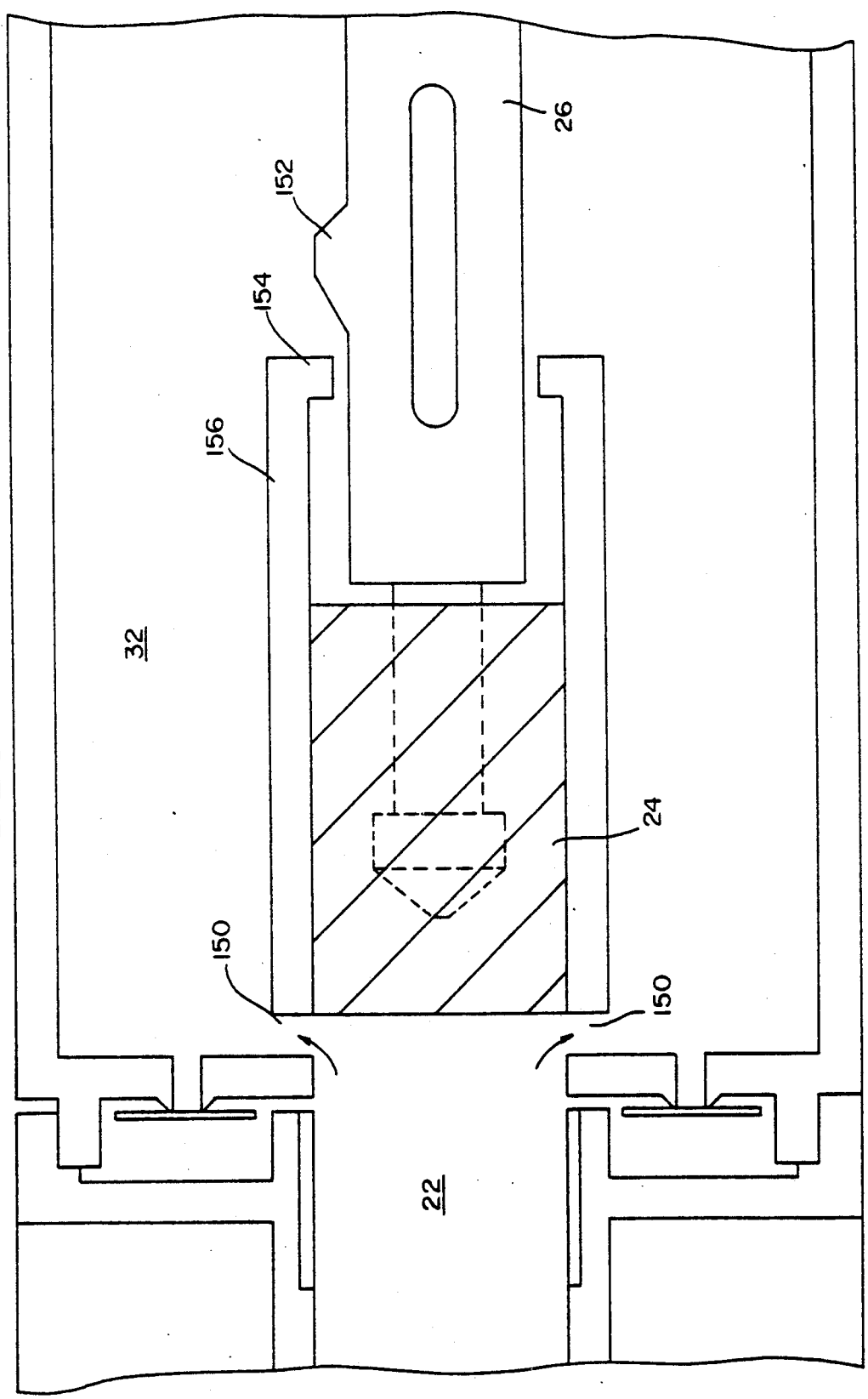

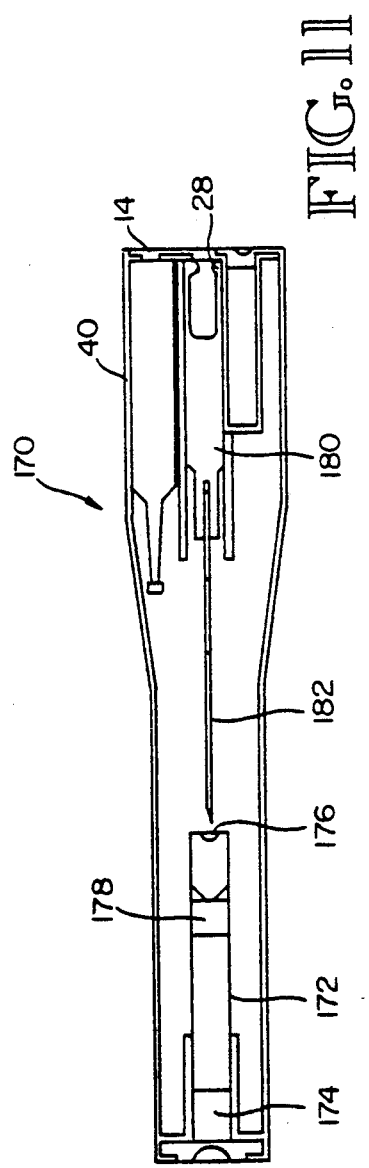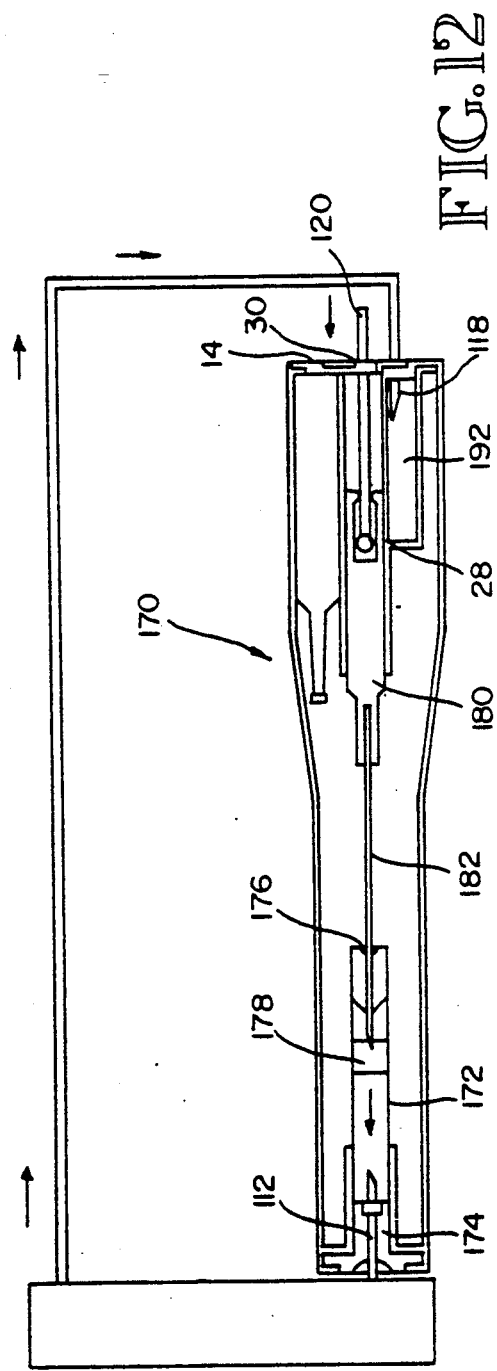

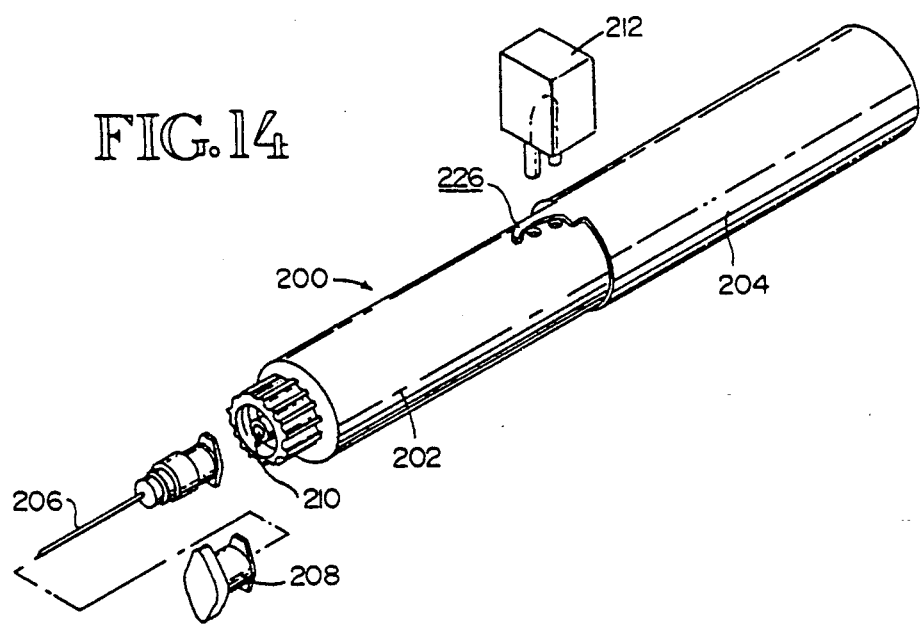
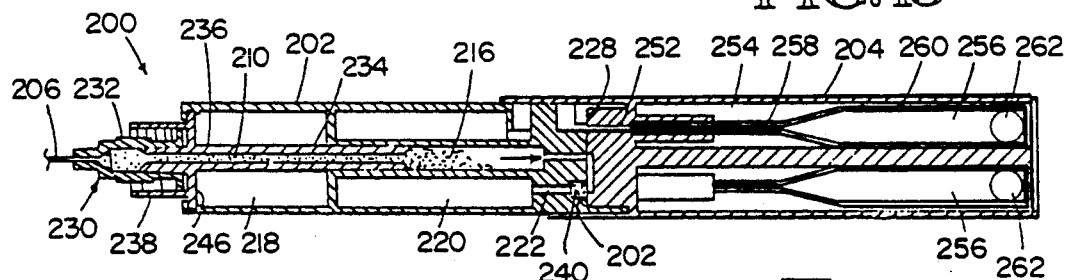
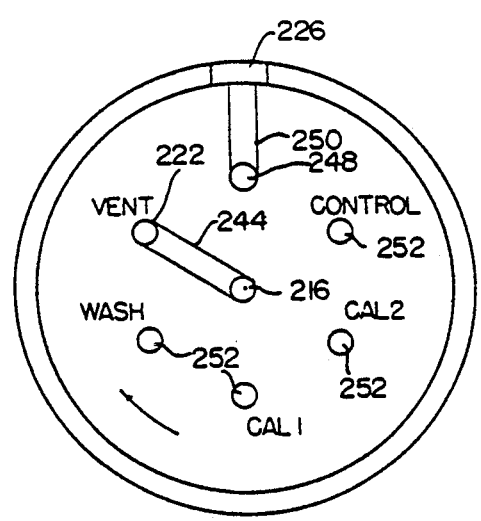
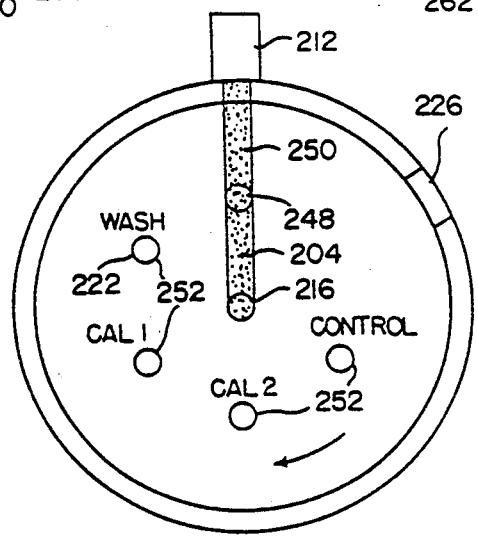

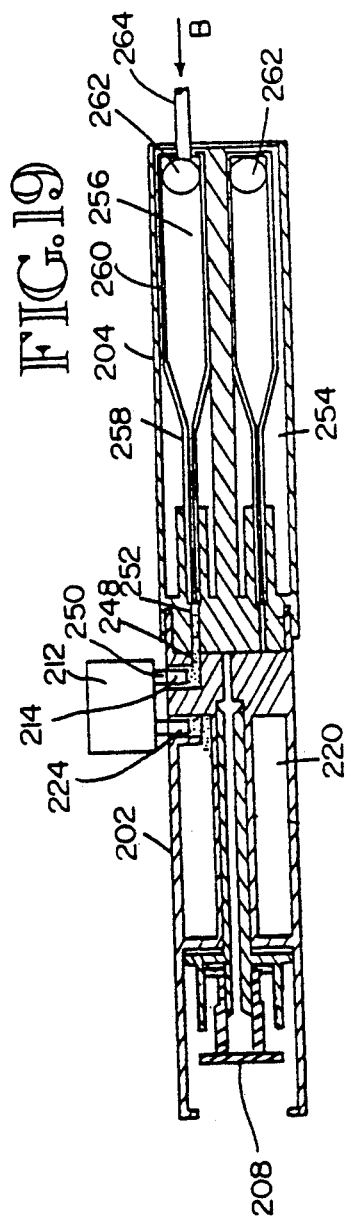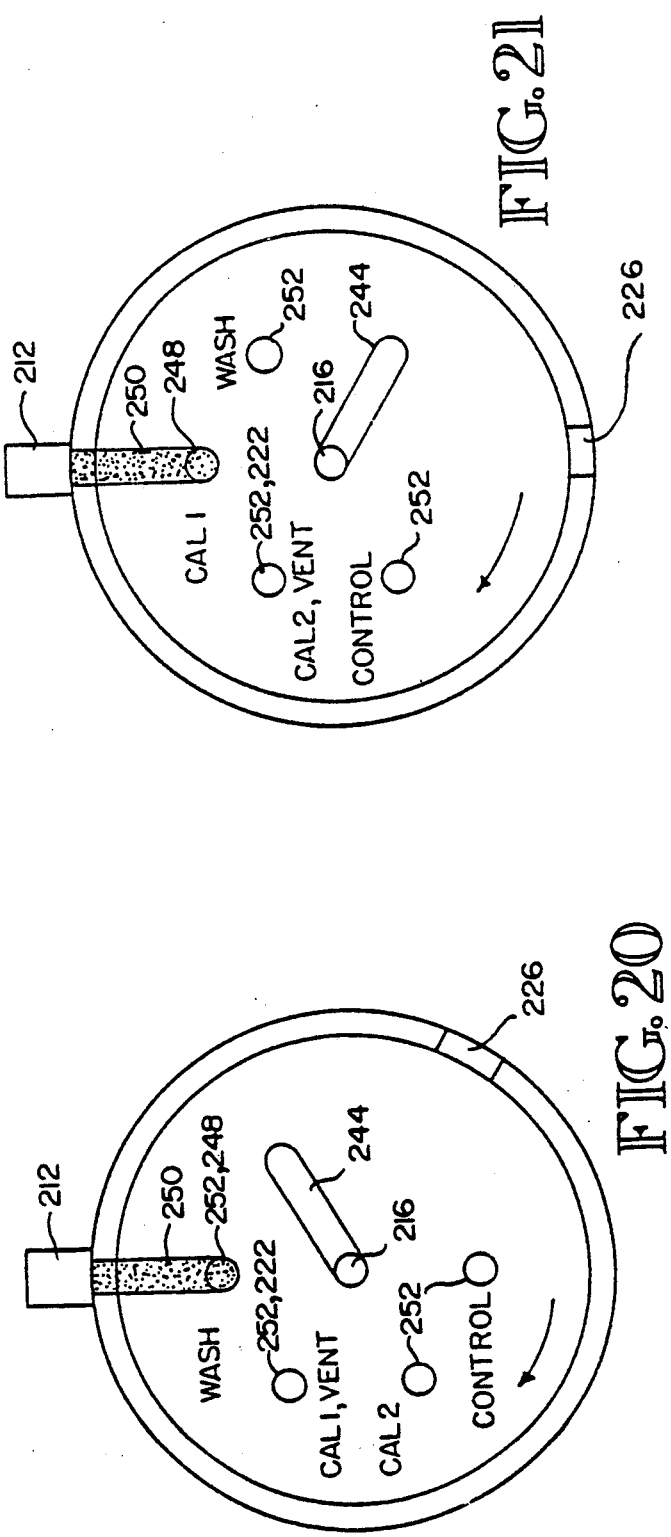

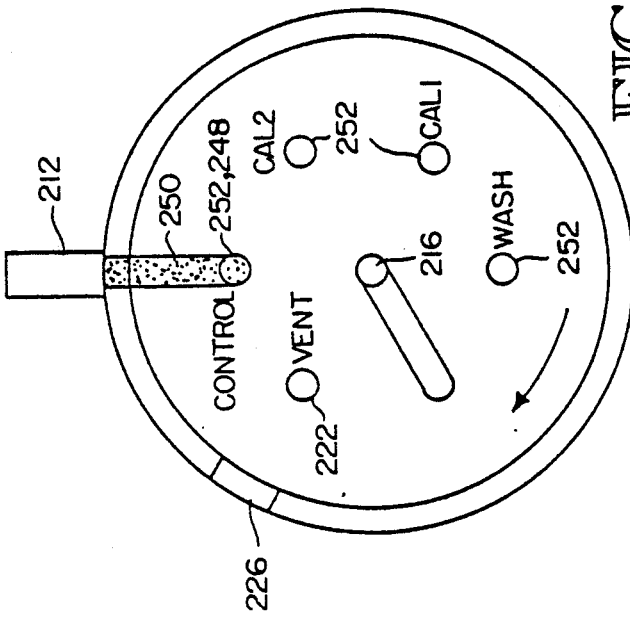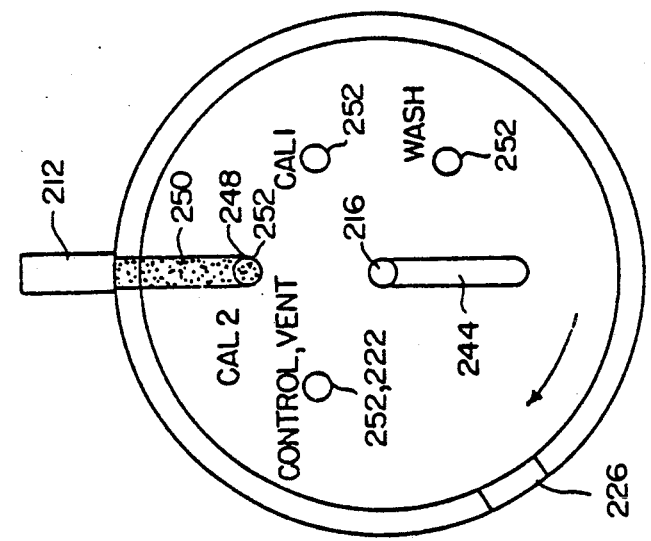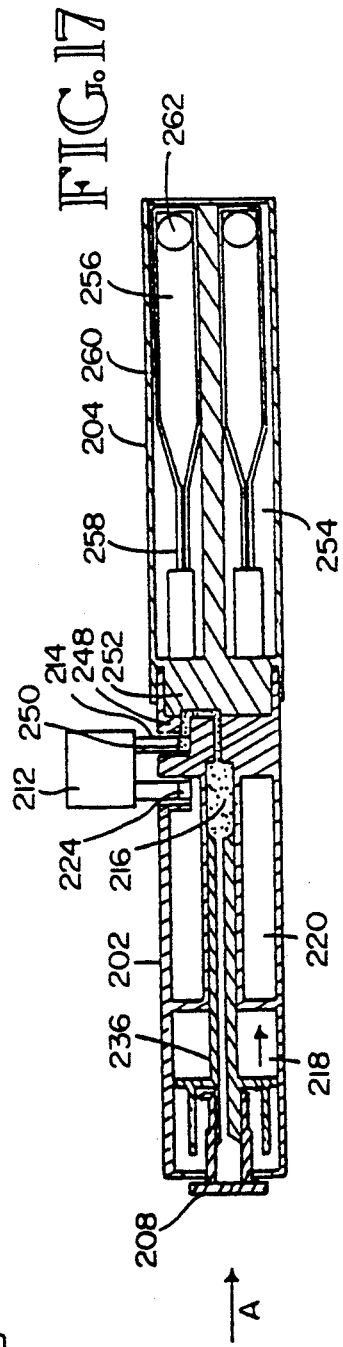

DISPOSABLE CARTRIDGE FOR SAMPLING AND ANALYZING BODY FLUIDS

CROSS-REFERENCE TO RELATED APPLICATIONS

This application is a continuation-in-part of U.S. patent application Ser. No. 528,801 filed May 24, 1990 and entitled Disposable Blood Sampling Cartridge, now abandoned.

DESCRIPTION

1. Technical Field

This invention relates to a device for collecting blood from blood vessels, for allowing the blood to be inexpensively and quickly analyzed, and for safely and easily collecting and disposing of waste blood and other fluids resulting from the analysis.

2. Background of the Invention

Conventional blood analyzing systems include a syringe into which the blood is collected, and an analyzer which analyzes the blood for such parameters as chemical composition, blood gas constituents, pH, etc. Two types of syringes have been used to take blood samples. The first type, which is used to sample arterial blood, includes a vented piston arrangement wherein a needle is inserted in a patient's artery, and the blood is forced into the syringe by the pressure differential between the absolute pressure in the artery and atmospheric pressure. In this first type, the air in the syringe is vented to the atmosphere as the syringe fills with blood since the vented piston allows air, but not blood, to pass. The second type of syringe includes a piston which is withdrawn to increase the volume in the syringe and thereby create a vacuum to suction the blood from the patient. This second type of syringe can be used to withdraw blood from a patient's artery or vein.

Venous blood samples are also commonly taken using a "VACUTAINER." A "VACUTAINER" is a device consisting of two components, namely an adapter having a double-ended needle and an evacuated test tube sealed with a resilient cap. The "VACUTAINER" is used by first inserting one end of the needle into a patient's blood vessel (usually a vein) and then puncturing the test tub's resilient cap with the other end of the needle. The vacuum in the test tube then draws blood through the needle and into the test tube. After sufficient blood has been drawn into the test tube, the needle is removed from the patient's blood vessel, and the test tube is separated from the adapter. The resiliency of the cap seals the puncture through the cap to prevent blood from leaking from the test tube and air from being drawn into the test tube.

Once the blood has been withdrawn from the patient into a syringe or test tube, the syringe or test tube is delivered to a lab for analysis. The sample blood is then introduced into a conventional blood analyzer. Conventional blood analyzers include a plurality of containers for respective calibrating or analyzing fluids, and a waste container for storing the waste fluids and blood. Additionally, special pre-analyzed control fluids must be analyzed frequently to verify analyzer calibration and proper operation.

One problem with conventional blood analyzers is that they are too large and expensive to be located at a patient's bedside. Accordingly, the blood sample must be sent to a central lab for analysis thereby requiring a relatively long period of time to obtain results. Under some circumstances, this delay can pose a serious threat to the health and safety of a patient since it may be necessary to delay corrective drug treatment or their procedures until the test results have been received. Additionally, conventional analyzers are relatively complex to operate, making bedside use impractical. For instance, the technician must insure that the analyzing fluids are not depleted.

The need to send a patient's blood sample to a location where a large number of other samples are being sent raises the obvious possibility that the patient's sample will become lost or incorrectly identified. Under these circumstances, an abnormality in the patient's blood could become misidentified with another patient so that the abnormality would go untreated. Also, the patient could receive treatment indicated by a lab report resulting from tests on another patient's blood, and such treatment would be wasteful and possibly harmful.

The disadvantages of the above, commonly used lab test procedures extend not only to the manner in which the blood samples are processed but also the manner in which the blood samples are handled and transported. The patient's blood sample can contaminate the health care practitioner or lab technician when the blood sample is being transported to the lab or transferred from the syringe or test tube to another container or to the instrument for analysis.

Additionally, current blood test procedures also provide an avenue for various errors or inaccuracies to enter into the testing procedure. For example, blood can be transferred from the syringe or test tube into a container that has been improperly or insufficiently cleaned. As a result, the blood sample can become contaminated with residue left in the container, thereby affecting the accuracy of tests performed on the sample. The blood sample can become contaminated upon exposure to air during this transfer as well. Although laboratory procedures have been designed to minimize this problem, any exposure to air during the transfer of the sample from the original collection container to a subsequent container or an analyzer may affect the accuracy of the analysis. Contaminants can also be present in the chemical analysis instruments that process the blood sample since the sample comes into contact with the same tubes, valves, pumps, etc., that the blood samples of other patients contact. In fact, it is quite common for deposits to build up in the flow path of the analysis instrument especially in valves and pumps. These deposits provide a ready vehicle for the growth of bacteria and the retention of blood samples or calibrating fluids from one sample to the next. Deposits on such components as valves can also cause them to stick either open or shut. While such flow path components as tubing, valves and pumps can be replaced whenever deposits start to build, frequent replacement of such components can be very expensive. The need to frequently monitor the condition of, and replace the components of, conventional blood chemical analyzing instruments can also be very time-consuming and thus diverts the attention of the health care practitioners from the care of patients.

To maintain and verify the accuracy of the analysis instruments can also be very time-consuming. Sensitive analysis instruments must be calibrated with numerous fluids and/or precision mixed gases at frequent intervals. To verify accuracy of calibration, samples with known results are frequently analyzed and the result recorded for statistical tracking. The calibration and verification procedures consume considerable additional time and require skilled operators. Considerable volumes of fluids and/or precision mixed gases are required to perform these operations. Since the flow path of these instruments can contain residual deposits from patient blood samples, all fluids utilized by the analyzer must be considered contaminated and be handled with as much caution as the original patient sample. Should any part of this calibration and verification process be skipped or performed incorrectly, the results could contain errors or inaccuracies that might adversely affect patient care.

Most of the above-described problems of conventional testing procedures could be eliminated if the blood sample was analyzed using a disposable device and an instrument located at the patient's bedside. However, bedside blood analysis was heretofore though not to be practical because the high cost and large size of conventional blood analysis instruments and associated fluid and/or gas containers prevented them from being either disposable or sufficiently portable to be effectively used at the patient's bedside.

Efforts have been made to simplify and miniaturize conventional analyzers by providing conventional analyzers with a disposable cartridge. The cartridge maintains the level of the analyzing fluids in the analyzer and provides a waste container for the waste analyzing fluids and blood. While such arrangement does simplify the analyzing procedure, the disposable cartridge is extremely expensive, making the device commercially impractical. Moreover, as with the conventional analyzer described above, a pumping system is required in the analyzer to pump the blood and analyzing fluids through the device, thereby adding both size and weight to the analyzer.

SUMMARY OF THE INVENTION

It is an object of the invention to provide a disposable blood sampling cartridge that also contains various fluids used in analyzing the blood.

It is another object of the invention to provide a disposable blood sampling cartridge that allows a blood sample to be analyzed in a manner that minimizes the dangers of contaminating the blood sample or medical personnel performing the analysis.

It is another object of the invention to provide a disposable blood sampling cartridge that allows the safe and easy disposal of the waste blood and other fluids used in the analysis.

It is another object of the invention to provide a disposable blood sampling cartridge that is capable of collecting venous blood without the use of a syringe.

It is another object of the invention to provide a device for collecting body fluids in a manner which does not require transfer from a collection device to another container in order to be analyzed.

It is still another object of the invention to provide a disposable blood sampling cartridge that forces collected blood, analyzing fluids and waste fluids through an analyzing device thus allowing the analyzing device to dispense with an expensive and difficult to clean fluid pump.

It is a further object of the invention to provide a disposable blood sampling cartridge that allows a blood sample analyzer to be inexpensive, compact and simple to use thereby making bedside blood analysis feasible.

These and other objects of the invention are provided by a disposable blood sampling cartridge for use with a blood sample analyzer. The blood sampling cartridge contains a blood reservoir having a first port adapted to communicate with a hypodermic needle. The cartridge also includes a waste collection chamber adapted to receive waste fluids from the blood sample analyzer, and a plurality of ampules each containing a respective fluid adapted for use by the blood sample analyzer. The cartridge is used by first inserting the hypodermic needle into a patient's artery or vein, and then drawing blood from the patient into the blood reservoir. The disposable blood sampling cartridge is then connected to the blood sample analyzer, and the blood is expelled from the reservoir into the analyzer. After the blood has been analyzed, it is transferred to the waste collection chamber in the cartridge. Each of the fluids in the blood collection cartridge are then expelled into the blood sample analyzer for use by the blood sample analyzer. After use, each of the fluids are also transferred to the waste collection chamber in the cartridge.

The blood reservoir in the cartridge is preferably vented through a port which is blocked by an air-permeable, blood-impermeable material so that blood flowing into the blood reservoir can displace air in the chamber through the material until the reservoir has been filled with blood. The cartridge preferably includes a piston that is movable into the blood reservoir to force blood out of the blood reservoir when the blood is to be analyzed. The piston is actuated externally through an aperture in the cartridge at one end of the cartridge. A plurality of ampules containing respective fluids used by the blood sample analyzer are also preferably accessible at the end of the cartridge containing the aperture. The fluid in the ampules are accessed through a frangible portion of a wall of each ampule that facing the end of the cartridge containing the aperture. As a result, the fluids in the ampules may be accessed by puncturing the ampules from the same end of the cartridge through which the piston is actuated.

The disposable blood sampling cartridge may include an evacuated container which is selectively coupled to the blood reservoir to draw blood into the blood reservoir thereby allowing the cartridge to be used for collecting venous blood. The evacuated container is preferably fabricated from a frangible material which is fractured by an externally accessible resilient tab positioned adjacent to the evacuated container thereby coupling the vacuum in the evacuated container to the blood reservoir. The tab may be forced inwardly by inserting the cartridge in a needle adapter containing a double-ended needle thereby causing the tab to fracture the evacuated container when one end of the needle is inserted into the blood reservoir and the other end of the needle is inserted into the vein of a patient.

Alternatively, the disposable blood sampling cartridge may include an evacuated cylinder having a puncturable septum at each end. The septum at one end is punctured by a needle adapter to draw blood into the evacuated cylinder. After sufficient blood has been drawn into the cylinder and the needle adapter has been removed, it is connected to a blood sample analyzer. The analyzer includes a hypodermic needle that punctures the septum through which the sample was taken to gain access to the interior of the evacuated cylinder. A second hypodermic needle mounted on a push rod in the cartridge is then actuated by an external actuating rod to puncture the septum at the opposite end of the evacuated cylinder. The point of the second needle is embedded in a breakaway piston positioned in the cylinder. As the push rod advances, the piston is pushed along the cylinder to force the blood out of the cylinder and into the analyzer. Thereafter, the second needle is pushed all of the way through the breakaway piston. The second needle has an outlet positioned in a waste collection chamber in the cartridge. The needle thus allows communication between the cylinder and the waste collection chamber. After the blood has been analyzed, it is forced into the waste collection chamber by analyzing fluids flowing from a plurality of ampules in the cartridge into the blood sample analyzer in the opposite direction. Spent analyzing fluids are also directed to the waste collection chamber in the same manner.

BRIEF DESCRIPTION OF THE DRAWINGS

FIG. 2 is a cross-sectional view of the blood sampling cartridge of FIG. 1 configured for taking a blood sample.

FIG. 4A is a cross-sectional view of the preferred embodiment of the inventive blood sampling cartridge used for sampling venous blood.

FIG. 4B is an end elevational view of the venous blood sampling cartridge of FIG. 4A.

FIG. 7 is a cross-sectional view showing the manner in which blood collected in the cartridges of FIGS. 1 and 4 are transferred into an external blood analysis device.

FIG. 8 is a cross-sectional view showing the manner in which various fluids stored in the cartridges of FIGS. 1 and 4 are transferred into an external blood analysis device.

FIG. 10 is a detailed cross-sectional view of a portion of the blood sampling cartridge of FIGS. 1 and 4 showing the manner in which waste blood and fluids flow into an internal waste collection chamber in the cartridge.

FIG. 11 is a cross-sectional view of an alternative embodiment of the inventive blood sampling cartridge used for sampling venous blood.

FIG. 12 is a cross-sectional view showing the manner in which venous blood collected in the cartridge of FIG. 11 is transferred into an external blood analysis device.

FIG. 14 is an isometric view of still another embodiment of the inventive disposable blood sampling cartridge shown with its internal rotary valve in the 0° position.

FIG. 15 is a cross-sectional view of the disposable cartridge taken along line 15—15 of FIG. 14.

FIG. 16 is a schematic, cross-sectional view of the disposable cartridge taken along line 16—16 of FIG. 15.

FIG. 17 is a cross-sectional view of the disposable cartridge taken along line 17—17 of FIG. 15 shown with its internal rotary valve in the 60° position.

FIG. 18 is a schematic, cross-sectional view of the disposable cartridge taken along line 18—18 of FIG. 17.

FIG. 19 is a cross-sectional view of the disposable cartridge taken along line 19—19 of FIG. 14 shown with its internal rotary valve in the 120° position.

FIG. 20 is a schematic, cross-sectional view of the disposable cartridge taken along line 20—20 of FIG. 19.

FIG. 21 is a schematic, cross-sectional view of the disposable cartridge taken along line 21—21 of FIG. 14 shown with its internal rotary valve in the 180° position.

FIG. 22 is a schematic, cross-sectional view of the disposable cartridge taken along line 22—22 of FIG. 14 shown with its internal rotary valve in the 240° position.

FIG. 23 is a schematic, cross-sectional view of the disposable cartridge taken along line 23—23 of FIG. 14 shown with its internal rotary valve in the 300° position.

DETAILED DESCRIPTION OF THE INVENTION

Figure 1:
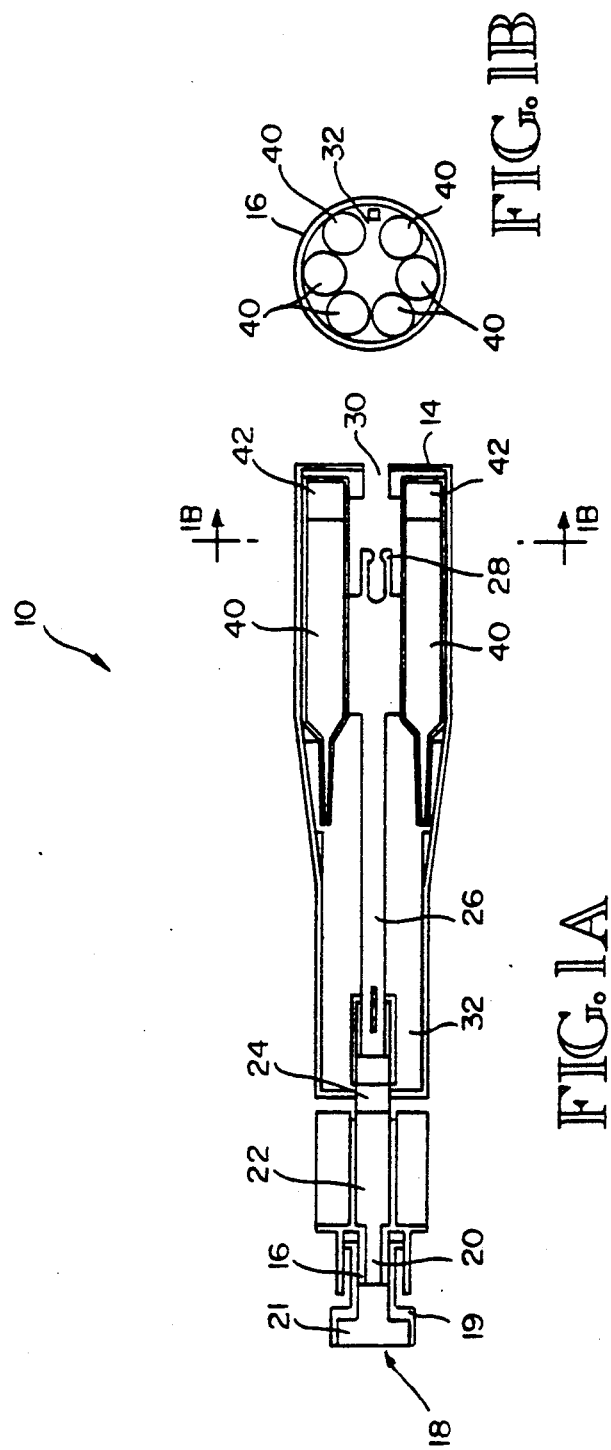
FIG. 1A is a cross-sectional view of the preferred embodiment of the inventive blood sampling cartridge used for sampling arterial blood.
FIG. 1B is a cross-sectional view of the blood sampling cartridge of FIG. 1A taken along the line 1B—1B of FIG. 1A.

One embodiment of the inventive disposable blood sampling cartridge 10 is illustrated in FIGS. 1A and 1B. The cartridge 10 illustrated in FIGS. 1A and 1B is specifically adapted to sample arterial blood. The cartridge 10 includes a generally cylindrical housing 12 having a generally planar end wall 14. A cylindrical boss 16 formed at the opposite end of the housing 12 is adapted to receive a hypodermic needle (not shown). However, during shipment and storage, the boss 16 is covered by a septum cap assembly 18. The septum cap assembly 18 includes a plastic cap 19 surrounding a resilient insert 21. The plastic cap 19 has a cylindrical portion 23 that fits over the boss 16.

The boss 16 defines a fluid port 20 communicating with a blood reservoir 22. The end of the blood reservoir 22 opposite the port 20 is closed by a piston 24 mounted at the end of a push rod 26. The opposite end of the push rod 26 includes a push rod clip 28 for releasably securing an actuating rod (not shown) extending through an aperture 30 in the end wall 14. The portion of the housing 12 surrounding the push rod 26 forms a waste collection chamber 32 which, as explained below, is used to collect waste fluids after the blood analysis has been completed. The housing 12 also contains a plurality of ampules 40 each of which contains a respective fluid that is used by an external blood sample analyzer. A piston 42 is formed at the end of each ampule 40 for expelling the fluid, as explained below.

Figure 3:
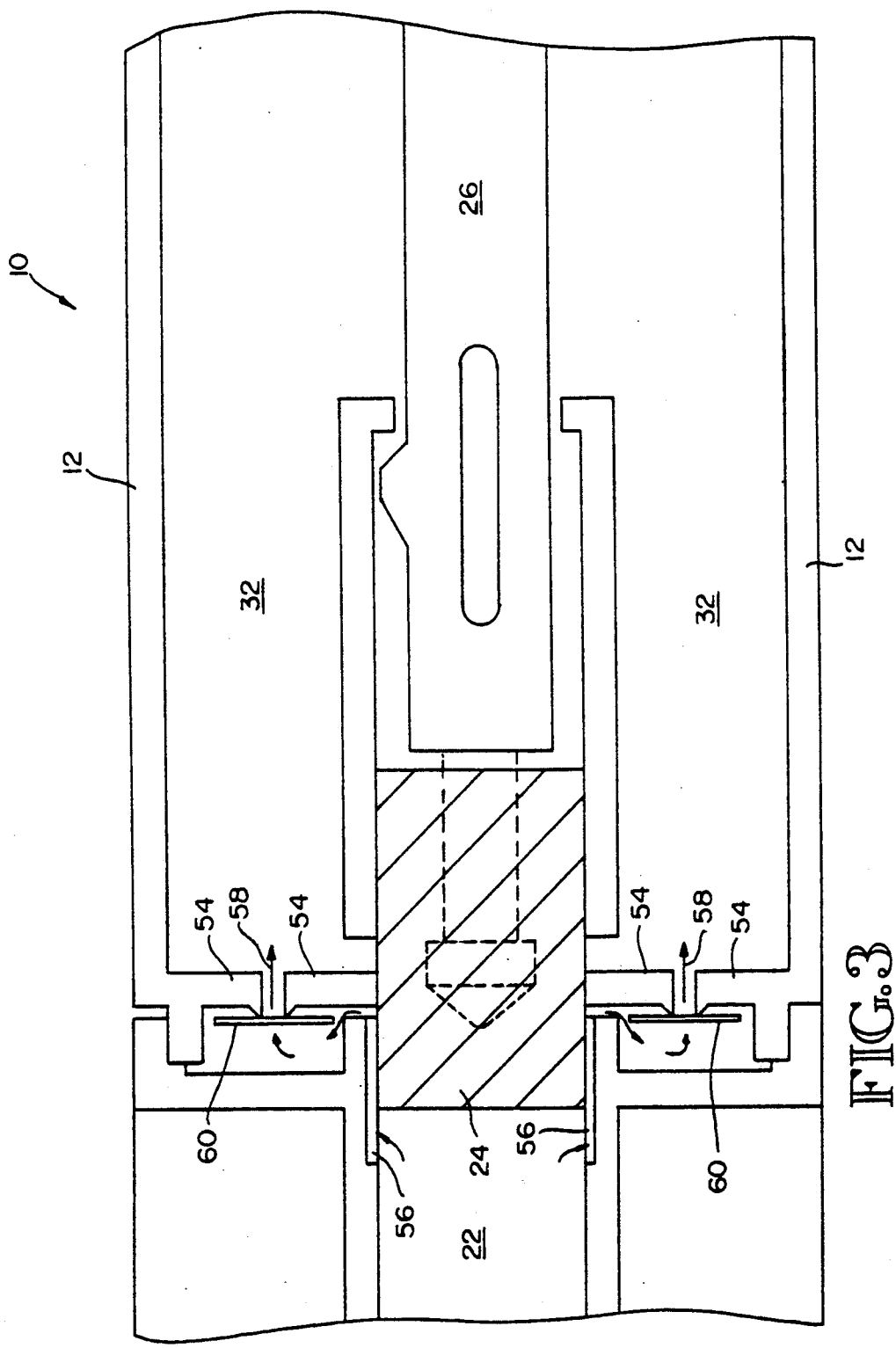
FIG. 3 is a detailed cross-sectional view of a portion of the blood sampling cartridge of FIG. 1 showing how an internal blood reservoir is vented during the blood collection process.

The blood sampling cartridge 10 is shown in FIGS. 2 and 3 in its configuration for taking a blood sample. With reference to FIG. 2, the septum cap assembly 18 (FIG. 1A) is removed from the boss 16 and a conventional hypodermic needle 50 is placed over the boss 16 in the same manner as the septum cap assembly 18. With reference also, now, to FIG. 3, the piston 24 is placed in a position so that it blocks communication between the blood reservoir 22 and the waste collection chamber 32. The piston 24 separates the blood reservoir 22 from the waste collection chamber 32 by virtue of the contact between the piston 24 and divider 54. However, the placement of the piston 24 forms a passage 56 around the piston 24 and through an opening 58 into the waste collection chamber 32. An air-permeable, fluid-impermeable membrane 60 is placed over the opening 58. As a result, when blood is forced into the blood reservoir 22 by arterial pressure, air in the blood reservoir 22 is vented through the passage 56 in opening 58 until the blood reservoir 22 has been filled with blood. The fluid-impermeable membrane 60 then prevents the blood from flowing from the blood reservoir 22 to the waste collection chamber 32. Once the blood reservoir 22 has been filled with blood, the cartridge 10 is ready to be connected to an external blood sample analyzer which analyzes the blood in the blood reservoir 22.

Figure 5:
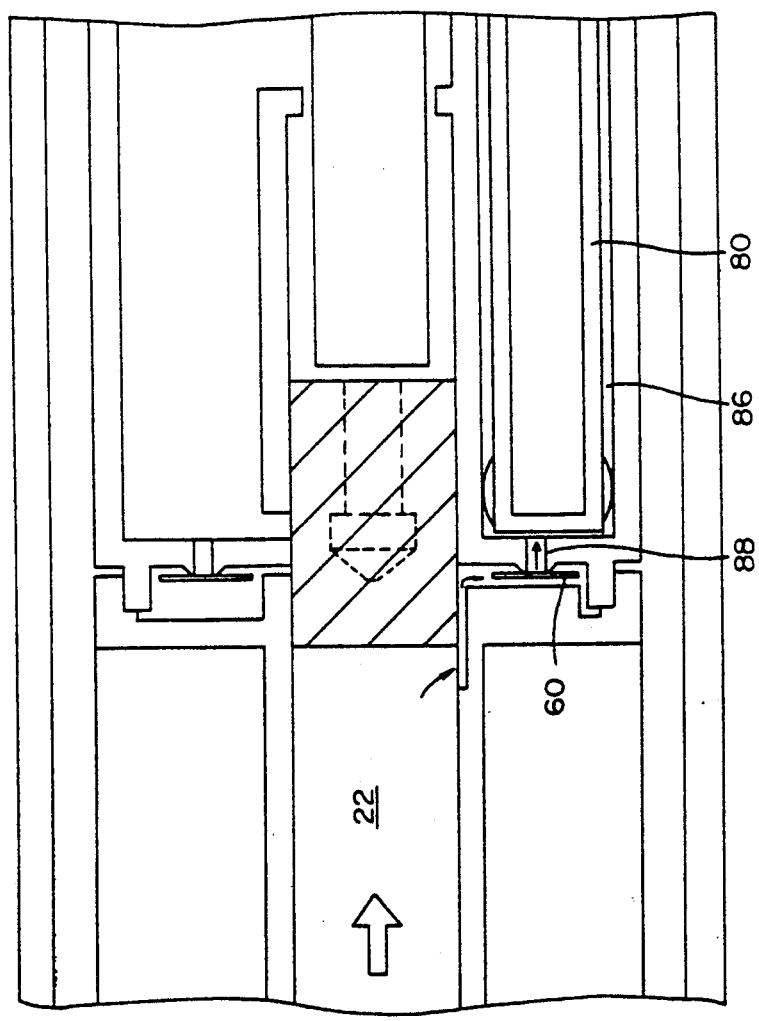
FIG. 5 is a detailed cross-sectional view of a portion of the venous blood sampling cartridge of FIG. 4 showing how a vacuum draws blood into an internal blood reservoir during the blood collection process.

As mentioned above, arterial blood is forced into the blood reservoir 22 in the embodiment of FIGS. 1-3 because the pressure of the blood in the arteries are greater than atmospheric pressure. However, the pressure of blood in veins, i.e., venous blood, is not sufficient to force venous blood into the blood reservoir 22. The disposable blood sampling cartridge 70 of FIGS. 4-7, which is substantially the same as the arterial sampling cartridge 10 of FIGS. 1-3, can be used to obtain samples of venous blood. Thus, for the sake of brevity, identical components have been provided with identical reference for both embodiments, and an explanation of their structure and operation will not be repeated. The venous blood sampling cartridge 70 of FIGS. 4-7 differs from the arterial blood sampling cartridge 10 shown in FIGS. 1-3 in two respects. First, its blood reservoir 22 is covered by a cap 72 made of a resilient material such as rubber. As explained below, the resilient composition of the cap 72 allows it to be punctured by a needle and causes it to be self-sealing when the needle is withdrawn. The second difference between the venous blood sampling cartridge 70 and the arterial blood sampling cartridge 10 is that the venous blood sampling cartridge 70 utilizes a vacuum to draw blood into the blood reservoir 22. Specifically, the venous blood sampling cartridge 70 contains a tube 80 made of a frangible material such as glass. The tube 80 is evacuated, and it is positioned within an airtight compartment 86, as best illustrated in FIG. 5. The airtight compartment 86 communicates with the blood reservoir 22 through an opening 88 and an air-permeable, fluid-impermeable membrane 60. Blood is drawn into the blood reservoir 22 of the venous blood sampling cartridge 70 by piercing the resilient cap 82 with a needle and then breaking the frangible tube 80, thereby coupling the vacuum in the tube 80 to the blood reservoir 22 through the opening 88. The vacuum draws blood into the blood reservoir 22 until the blood reservoir 22 is filled, at which point the fluid-impermeable membrane 60 prevents further blood from entering the reservoir 22.

Figure 6:
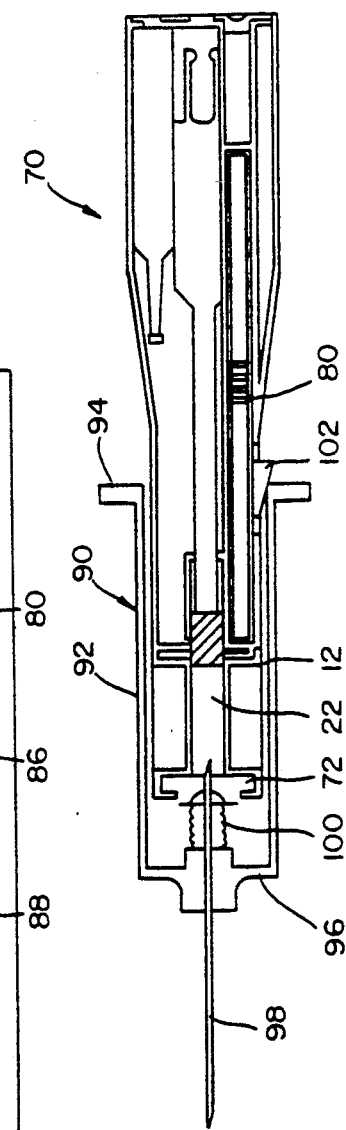
FIG. 6 is a cross-sectional view of the venous blood sampling cartridge of FIG. 4 configured for taking a blood sample.

Although any suitable means may be used to pierce the cap 72 and break the tube 80, a needle adapter 90 illustrated in FIG. 6 is preferably used to perform both functions. The needle adapter 90 is formed of a rigid material, such as plastic. The needle adapter 90 has a cylindrical portion 92 having an outwardly extending radial flange 94 at one end and an end cap 96 formed at the opposite end. The end cap 96 carries a double-ended hypodermic needle 98, the inner end of which extends through a resilient seal 100. The inside diameter of the cylindrical portion 92 is just slightly larger than the outside diameter of the housing 12. As a result, when the cartridge 70 is inserted into the needle adapter 90, as illustrated in FIG. 6, the inner portion of the needle 98 pierces the resilient cap 72. At the same time, the flanged end of the adapter 90 pushes a tab 102 inwardly against the frangible tube 80, thereby fracturing the tube 80 and releasing its vacuum to the blood reservoir 22.

In practice, the cartridge 70 is not inserted into the needle adapter 90 a sufficient distance to depress the tab 102 until the forward end of the needle 98 has been placed in the vein of a patient. Once the needle 98 is in place, the cartridge 70 is inserted further into the needle adapter 90 to depress the tab 102 to break the tube 80 and draw blood from the vein into the blood reservoir 22. Once the blood has been drawn into the blood reservoir 22, it is processed in the same manner as the blood in the arterial blood sampling cartridge 10 is processed.

The housing 12 surrounding the blood reservoir 22, as well as the blood reservoir 22 itself, is preferably made from a transparent material, such as glass or clear plastic. As a result, the medical practitioner taking the blood sample can view the blood flowing into the blood reservoir 22. Also, the blood reservoir 22 preferably contains an anticoagulating agent, such as heparin, to prevent the blood sample from coagulating in the blood reservoir 22.

Although the various embodiments of the inventive disposable blood sampling cartridge have been described as using a hypodermic needle inserted into a blood vessel to obtain blood samples, it will be understood that other devices may be used. For example, a hypodermic needle may be inserted into a catheter inserted in a blood vessel, a conduit delivering blood to a hemodyalysis device, an arterial line, etc.

The disposable blood sampling cartridge 10 is connected to a blood sample analyzer, such as a flow cell 110, as illustrated in FIG. 7. It will be understood, however, that other embodiments of the inventive blood sample cartridge, including the cartridge 70, are connected to the flow cell 110 in the same manner. Fluid can flow through the flow cell 110 in either direction through first and second conduits 112, 114. Each of the conduits 112, 114 terminate in respective hypodermic needles 116, 118, respectively.

The blood sampling cartridge 10 is connected to the flow cell 110 with the needle 116 extending through the resilient insert 21 of the septum cap assembly 18 (or cap 72 of the venous blood sampling cartridge 70) and into the blood reservoir 22. The cartridge 10 is rotated so that the waste area 32 is opposite the needle 118 of the conduit 114, and the needle 118 is then inserted through the end 14 of the housing 12 into the waste area 32. An actuating rod 120, which may be a part of the blood sample analyzer, is then inserted through the aperture 30 in the end wall 14 to engage the clip 28 at the end of the push rod 26. The actuating rod 120 then forces the push rod 26 forwardly so that the piston 24 is pushed into the blood reservoir 22. The piston 24 forces blood from the blood reservoir 22 through the conduit 112 into the flow cell 110. The blood flowing into the flow cell 110 displaces any analyzing fluid still in the flow cell 110 from a previous test. This remaining analyzing fluid flows through conduit 114 into the waste collection chamber 32. A small air bubble, which naturally occurs as the needles 112, 118 are inserted and removed from the cartridge 10, is introduced ahead of the blood, and aids in maintaining the separation between the blood and the analyzing fluid left from the previous test. The bubble thus prevents the blood from mixing with the fluid.

When the actuating rod 120 has reached the end of its travel, the flow of blood from the blood reservoir 22 terminates and the flow cell 110 analyzes the blood. After the analysis has been completed by the flow cell 110 in a conventional manner, the needle 118 is withdrawn from the end wall 14 of the cartridge 10, and the cartridge 10 is rotated to the position shown in FIG. 8. In this position, the needle 118 is inserted through the end wall 14 of the housing into one of the ampules 40 contained within the housing.

Figure 9A:
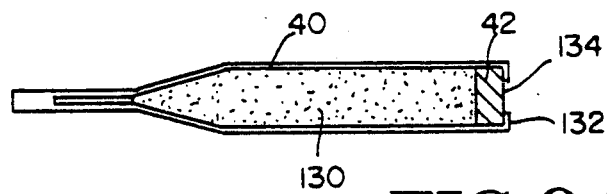
FIGS. 9A-D are cross-sectional views showing how fluids in respective ampules contained in the blood sampling cartridges of FIGS. 1 and 4 are accessed.
Figure 9B:
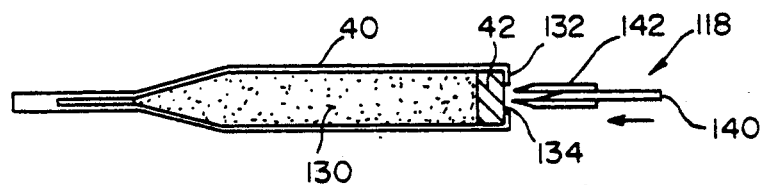
Figure 9C:
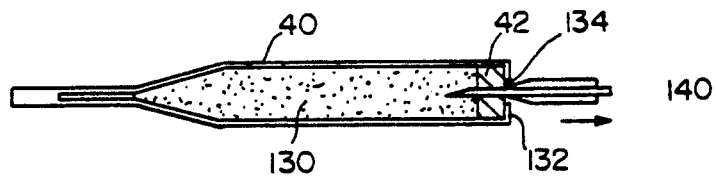
Figure 9D:
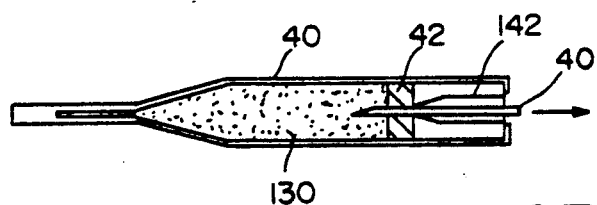

The end wall of the ampule 40 may be broken and the analyzing fluid extracted by any suitable means. However, in the preferred embodiment, the technique illustrated in FIG. 9 is used. Specifically, as shown in FIG. 9A, the ampule 40 containing analyzing fluid 130 has its internal piston 42 positioned against an end wall 132 having a thinned portion 134. As shown in FIG. 9B, the needle 118 includes a hollow inner needle 140 and an outer sleeve 142 slideably mounted on the inner needle 140. The sleeve 142 is pushed against the thinned portion 134 of the end wall 132 in order to crack the thinned portion 134 as illustrated in FIG. 9B. The inner needle 140 is then pushed through the piston 42 as illustrated in FIG. 9C. Finally, the inner needle 140 and outer sleeve 142 are advanced into the ampule 40 together, thereby driving the piston 42 further into the ampule 40. Movement of the piston 42 displaces the fluid 130 into the inner needle 140 and on the conduit 114 to the flow cell 110 as illustrated in FIG. 8.

Although the flow cell 110 has been described as using a needle 118 having an inner needle 140 and an outer sleeve 142 to puncture the ampules 40, other devices can be used. For example, a pointed rod may be used to puncture the ampule 40, and a separate hollow needle may be used to draw analyzing fluid from the ampules 40. Also, an ampule having a resilient, easily punctured end wall may be used.

Returning now to FIG. 8, as the piston 42 is pushed into the ampule 40, the actuating rod 120 pulls the push rod 26 rearwardly until the piston 24 has been withdrawn to the position illustrated in FIG. 8. The actuating rod 120 is then pulled from the clip 28 and out of the aperture 30, as illustrated in FIG. 8. As the piston 24 is pulled out of the blood reservoir 22, it creates a suction in the blood reservoir 22 that aids in withdrawing the sampled blood from the flow cell 110 to the conduit 112. The fluid flowing into the flow cell 110 through the conduit 114 also, of course, forces the analyzed blood out of the flow cell 110. When the piston 24 has been fully retracted, it allows free communication between the blood reservoir 22 and the waste collection chamber 32, as illustrated in FIG. 10. Specifically, when the piston 24 has been fully retracted, its side walls no longer make contact with the divider 54, as illustrated in FIG. 3. Consequently, fluid can flow from the blood reservoir 22 into the waste collection chamber 32 around the piston 24 through path 150. As also illustrated in FIG. 10, the push rod 26 has formed therein an outwardly extending tab 152 which is captured by an inwardly extending ring 154 mounted at the end of a resilient finger 156 when the push rod 26 is in the position illustrated in FIG. 3. Withdrawal of the push rod 26 to open the path 150 between the blood reservoir 22 and the waste collection chamber 32 requires that the projection 152 displaces the ring 154. The projection 152 and ring 154 thus provide a detent for preventing the path 150 between the blood reservoir 22 and waste collection 32 from being inadvertently opened.

Once the path 150 has been opened, the analyzed blood can flow from the blood reservoir 22 into the waste collection chamber 32. The analyzing fluid extracted from the ampule 40 then flows into the flow cell 110 through the conduit 114. When all of the fluid 130 has been removed from the ampule 40, the needle 118 is withdrawn from the housing 12. The cartridge 10 is then rotated until the needle 118 is positioned behind another ampule 40. The procedure shown in FIG. 8 is then repeated to cause the fluid from the next ampule to flow through conduit 114 into the flow cell 110, thereby forcing the previously withdrawn fluid into the waste collection chamber 32 through the needle 112, blood reservoir 22, and path 150. Fluid is withdrawn from each of the ampules in the same manner until the blood sample analyzer has completed its analysis.

As is well known in the art, blood sample analyzers, such as the flow cell 110 illustrated in FIG. 8, utilizes several fluids for performing such functions as calibrating the unit and washing the unit to prevent contamination from prior calibrating fluids and blood samples.

After the analysis has been completed, the needles 112, 118 are withdrawn from the cartridge 10 and the cartridge 10 is discarded. Significantly, all of the waste products from the analysis are also discarded with the cartridge 110.

Figure 13:
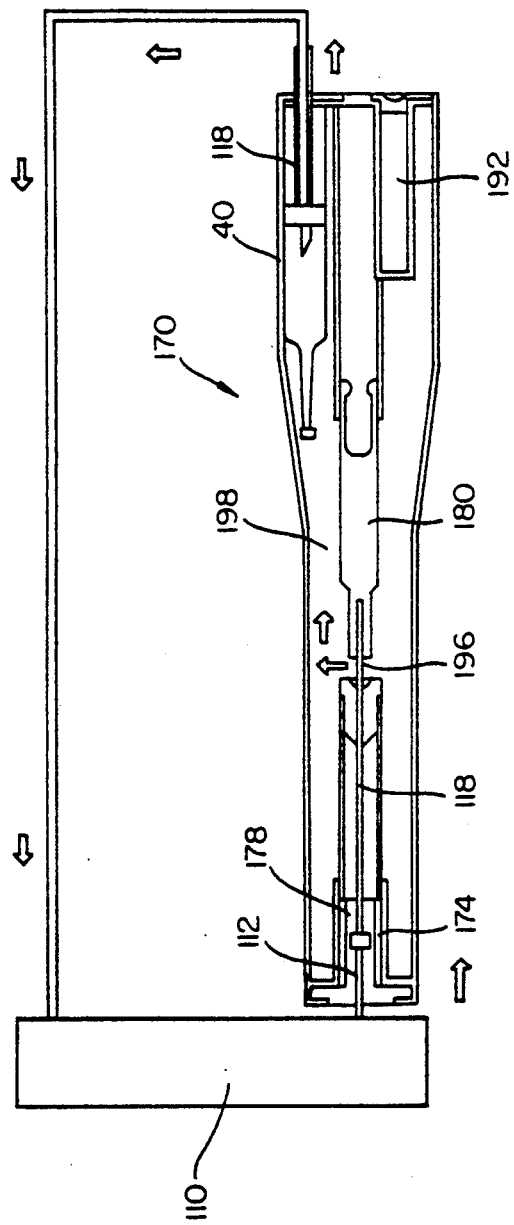
FIG. 13 is a cross-sectional view showing the manner in which various fluids stored in the cartridge of FIG. 11 is transferred into an external blood analysis device.

An alternative embodiment of a venous blood sampling cartridge 170 is illustrated in FIGS. 11-13. As with the previously explained embodiments, the cartridge 170 includes a housing 12 containing a plurality of fluid ampules 40 which are accessed through the end wall 14 of the housing 12. However, the venous blood sampling cartridge 170 illustrated in FIGS. 11-13 contains an evacuated blood collection tube 172 having septums 174, 176 at opposite ends and a breakaway piston 178 of the same type 42 used in the ampules 40, as explained above. The cartridge 170 also utilizes a push rod 180 having a clip 28 formed at one end adjacent in aperture 30 in the end wall 14. However, a hypodermic needle 182 projects from the opposite end of the push rod 180.

The blood sampling cartridge 170 is used to take a sample of venous blood in substantially the same manner as the previously described venous blood sampling cartridge 70 explained above with respect to FIG. 6. Specifically, a needle adapter having a double-ended needle is placed in the vein of a patient and then pierces the septum 174 of the blood collection tube 172. The vacuum in the tube 172 then draws venous blood into the tube 172. When sufficient blood has been drawn into the tube 172, the double-ended needle is pulled out of the blood vessel and out of the septum 174.

The tube 172 is preferably formed from a transparent material, such as glass or transparent plastic, so that the person taking the sample can determined when it has received sufficient blood. Also, the tube 172 preferably contains an anti-coagulating agent.

After the blood sample has been taken, the cartridge 170 is connected to a blood sample analyzer, such as a conventional flow cell 110 as illustrated in FIG. 12. As with the previously explained embodiments, the flow cell 110 includes a needle 112. The needle pierces the septum 174 while the needle 118 at the end of the conduit 114 is inserted through the end wall 14 of the cartridge 170 into a first waste collection area 192. The actuating rod 120 is then inserted through the aperture 30 and into the clip 28 of the push rod 180. The actuating rod 120 advances the push rod 180, thereby driving the needle 182 through the septum 176 and into the breakaway piston 178. However, the breakaway septum 178 has sufficient resistance to puncture that the needle 182 slides the piston 178 along the blood collection cylinder 172 rather than puncturing the piston 178. As the piston 178 slides along the blood collection tube 172, it forces the blood in the tube 172 into the flow cell 110 which, in turn, forces fluids from a previous test through the conduit 114 in needle 118 into the waste collection chamber 192.

When the piston 178 has reached the opposite end of the tube 172, all of the blood has been ejected from the tube 172 and further movement of the piston 178 is not possible. As the push rod 180 is advanced further, the needle 182 is pushed all the way through the piston 178, as illustrated in FIG. 13. The needle 118 is then withdrawn from the waste collection chamber 192 and inserted into one of the ampules 40, as explained above with reference to FIG. 8. The needle 118 includes a port 196 which opens into a second waste collection chamber 198. The needle 118 is then in communication with the needle 112 so that analyzed blood and used analyzing fluids flow from the flow cell 110 and conduit 112 through the needle 118 and out port 196 into the second waste collection chamber 198. After all of the ampules 40 in the cartridge 170 have been emptied as described above, the needles 112, 118 are removed from the cartridge 170 and the cartridge 170 is discarded.

As shown in FIG. 14, an alternative embodiment of a disposable arterial blood sampling cartridge 200 including front 202 and rear 204 cylindrical portions. A needle 206 projects from the front portion 202, and the front and rear portions 202, 204, respectively, are rotatable with respect to each other. A cap 208 is also shown for covering a blood inlet 210 of the front portion after the blood has been withdrawn and the needle removed. As explained below, rotation of the front and rear portions 202, 204 with respect to each other between each of several discrete positions controls:
 (a) the flow of blood
   (i) through the needle 206 into the front portion 202;
   (ii) from the front portion 202 to a flow cell 212 through an outlet port 214; and
 (b) the flow of waste blood, calibrating, control and washing fluids from respective reservoirs in the rear portion 204 to the flow cell 212 through the outlet port 214 and into the waste chamber in the front portion 202.

The flow cell 212 is of conventional design and, taken alone and apart from the blood sampling device 200, is not considered to be inventive.

Referring also now to FIG. 15, the front portion 202 includes a blood reservoir 216 connected to the needle through the blood inlet 210, a piston receiving portion 218, an annular waste chamber 220, a vent line 222 communicating with the waste chamber, and cartridge outlet and inlet ports 214, 224, respectively. The ports 214, 224 are normally closed by a cover 226 that projects forwardly from the rear portion 204. The blood reservoir 216, vent line 222 and cartridge outlet port 214 each have a longitudinal portion which communicates with a rear face 228 of the front portion 202. In particular, the blood reservoir 216 is disposed directly on the longitudinal axis of the front portion 202 while the vent line 222 and cartridge outlet port 214 are radially displaced from the longitudinal axis by an equal distance. The needle unit 230 includes a needle 206 as well as a needle attaching portion 232. The needle attaching portion 232 is designed to be slid onto one end of the tubular portion 234 of the piston unit 236 such that the drive hex 238 circumscribes the needle attaching portion in the manner illustrated in FIG. 15.

Referring also to FIG. 16, the vent line 222 has a vent 240 disposed therein which permits air to pass therethrough while preventing the passage of blood. Natural venting is provided through the cartridge inlet port 224 when blood is withdrawn and through the vent line 222 when waste fluids are introduced into the waste chamber 220.

The rear portion 204 is also cylindrical in shape and has a diameter slightly larger than the diameter of the front portion 202. In this manner, a front end of the rear portion 204 is rotatably disposed over the rear end of the front portion 202 such that the front face 242 of the rear portion abuts against the rear face 228 of the front portion 202, as illustrated in FIG. 15. A groove 244 is provided on the front face 242 of the rear portion. The groove 244 extends radially from the center of the face, terminating short of the outer circumference of the rear portion 204. The groove is designed to interconnect the blood reservoir 216 of the front portion 202 to either the vent line 222 (FIGS. 16 and 17) or the cartridge outlet port 214 by rotating the front portion 202 relative to the rear portion 204, as will be described in detail below.

The piston unit 236 includes an axially extending tubular portion 234, flange 246 and drive hex 238, as illustrated in FIG. 16. The tubular portion 234 defines the blood inlet 210 which communicates with the blood reservoir 216 of the front portion 202. The tubular portion 234 is telescopically disposed in the bore forming the blood reservoir while the flange 246 is slidably disposed in the piston receiving portion 218 of the front portion. The piston unit 236 is actuated to expel blood from the blood reservoir 216, as described in detail below.

As illustrated in FIG. 19, the cartridge outlet port 214 is substantially L-shaped having the above-described longitudinal portion 248 as well as a radially extending portion 250 which extends to the outer circumference of the front portion. The cartridge inlet port 224 also extends in the radial direction and communicates with the waste chamber 220. The inlet port 224 is disposed adjacent the outlet port 214 allowing convenient access of the flow cell to the ports.

With reference to FIGS. 15 and 16, the rear portion 204 includes four axially extending ampule ports 252 and a corresponding number of ampule receiving bores 254. Each of the ampules 256 includes a small diameter stem portion 258 and a large diameter base portion 260. The ampules are respectively disposed in the ampule receiving bores by respectively inserting the small diameter portions in the ampule ports. Each of the ampules contains a different analyzing fluid: wash, calibrant 1, calibrant 2, and control. The analyzing fluids are utilized to wash, calibrate, and flush the flow cell 212 during the blood analysis. The ampule ports 252 communicate with the front face 242 of the rear portion 204 and are sequentially aligned with the longitudinally disposed portion 248 (FIG. 20) of the cartridge outlet port 214 such that the ampule fluids can be individually introduced into the flow cell 212 by successively rotating the front portion with respect to the rear portion of the device a predetermined number of degrees.

Each of the ampules 256 has a ball 262 which acts as a piston to pump the fluid therefrom. Specifically, as illustrated in FIG. 19, the rear of each ampule is fractured using push rod 264 enabling the push rod 264 to slide the ball in the direction of the ampule stem 258, as illustrated by the arrow. In this manner the fluids are pumped from the ampules into the flow cell via the ampule ports 252 and the outlet port 214.

The volume of the blood reservoir is relatively small so as to minimize the amount of blood withdrawn from the patient. Correspondingly, the passages in the cartridge are designed to be relatively short in length and small in diameter to insure that a minimal amount of blood is lost when the blood flows into the flow cell so that there is a sufficient amount of blood in the flow cell for analysis. Additionally, the front portion 202 may be manufactured out of a transparent material to permit the user to view the amount of blood in the reservoir. Finally, an absorbent material may be packed in the waste chamber to absorb the waste fluids.

The operation of the device is as follows. Initially, the front portion 202 and rear portion 204 are rotatably aligned in the manner illustrated in FIGS. 14, 13 and 16 with the cover 226 blocking the flow cell ports 214, 224. For explanation, this position will be referred to as the 0° position. In the 0° position, blood is withdrawn from the patient's artery, relying on the arterial pressure to force the blood into the device. As illustrated in FIGS. 15 and 16, the blood reservoir 216 of the front portion 202 is connected to the vent line 222 via the groove 244 for permitting the air in the blood inlet to be vented through the waste chamber 220 so as to allow the blood to enter the device. Once the flow of blood reaches the vent 240 provided at the inlet to the vent line 222 the flow of blood from the patient's artery stops.

Thereafter, the needle is withdrawn from the patient, removed from the device and a luer lock cover 208 (FIG. 17) secured to the front end of the piston unit 236. The device is then placed in an analyzer having a flow cell 212 (FIG. 14). The analyzer rotates the rear portion 204 of the device approximately 40° with respect to the front portion 202 to expose the flow cell ports 214, 224. At this position, the flow cell 212 in the analyzer is mated to the outlet and inlet ports 214, 224, respectively. Thereafter, the rear portion is rotated an additional 20° to the 60° position to align the groove 244 with the longitudinal portion 248 of outlet port 214, as illustrated in FIGS. 17 and 18. In this position, the blood reservoir 216 communicates with the outlet port 214 through the groove 244, longitudinal portion 248 and radially extending portion 250. At this time, the analyzer slides the piston unit 236 in the direction of the arrow of FIG. 17 a predetermined distance causing the blood in the blood reservoir 216 to be introduced into the flow cell. Thereafter, the blood is analyzed.

After the blood has been analyzed, the analyzer rotates another 60° to the 120° position, as illustrated in FIGS. 19 and 20. In this position, the ampule port 252 for the wash is aligned with the longitudinal portion 248 of the cartridge outlet port 214. At this time, a mechanism in the analyzer fractures the stem 258, the push rod 264 in the analyzer fractures the base of the ampule and, thereafter, the push rod 264 pushes the piston ball 262 in the direction illustrated by arrow B in FIG. 19 forcing the wash fluid from the ampule and into the flow cell 212. The wash fluid thereby flushes the blood from the flow cell through the cartridge inlet port 224 and into the annular waste chamber 220. Thereafter, the rear portion 204 is rotated another 60° to the 180° position, illustrated in FIG. 21, aligning the calibrant 1 ampule port 252 with the longitudinal portion 248 of cartridge outlet port 214. Again, the ampule stem and base are fractured and the calibrant 1 fluid forced into the flow cell to calibrate the analyzer and flush the wash fluid from the flow cell and into the waste chamber 220. These steps are repeated for the calibrant 2 ampule at the 240° position (FIG. 22) and the control ampule at the 300° position (FIG. 23). Finally, after the control fluid has been introduced into the flow cell 212, the analyzer rotates the rear portion another 20° to the 320° position and detaches the cartridge from the flow cell. Thereafter, the analyzer rotates the rear portion another 40° to the initial 0° position such that the cover 268 of the rear portion 204 closes the flow cell ports 214, 224, as illustrated in FIGS. 14 and 16. The device can then be disposed of without the user ever contacting the blood or any of the fluids.

While the various embodiments of the invention have been described with the disposable cartridge storing four ampules, it is understood that the cartridge could store fewer or more ampules as required. Moreover, while the various embodiments of the disposable cartridge are shown connected to a flow cell for analyzing blood, it is understood that the cartridges could be used to obtain samples of other body fluids, which would then be analyzed by analyzers other than flow cells or other types of blood sample analyzers.

We claim:

1. A method of analyzing a body fluid of a patient using a body fluid analyzer and a disposable sampling cartridge containing a body fluid reservoir, a first port communicating with said body fluid reservoir, a waste collection chamber, and at least one analyzing fluid adapted for use by said body fluid analyzer, said method comprising:
    drawing a body fluid from the patient into said body fluid reservoir;
    connecting said disposable sampling cartridge to said body fluid analyzer and expelling said body fluid from said reservoir into said body fluid analyzer;
    analyzing said body fluid in said body fluid analyzer;
    expelling said analyzing fluid from said sample collection cartridge into said body fluid analyzer for use by said body fluid analyzer either before or after said body fluid has been expelled from said reservoir into said body fluid analyzer;
    before or after said body fluid and said analyzing fluid have been expelled from disposable sampling cartridge into said body fluid analyzer, conveying fluid from said body fluid analyzer to said waste collection chamber; and
    disconnecting said sampling cartridge from said body fluid analyzer.

2. The method of claim 1 wherein said analyzing fluids are contained in respective ampules each containing a piston member, said ampules being circumferentially spaced about the central axis of said cartridge, and wherein said analyzing fluids are successively expelled from said ampules by rotating said cartridge to successively align each of said ampules with an actuating rod, and by then forcing said actuating rod into the aligned ampule to displace said piston member and expel said analyzing fluid from said ampule.

3. The method of claim 2 wherein said ampules are fabricated with a frangible wall, and wherein said actuating rod is forced through said frangible wall to make contact with said piston member.

4. The method of claim 3 wherein said actuating rod includes a hollow shaft surrounded by a concentric cylinder, and wherein said analyzing fluids are expelled from said ampules by forcing said hollow shaft through said piston member into said analyzing fluid and then forcing said concentric cylinder against said piston member to slide said piston member along said ampule thereby forcing said analyzing fluid out of said ampule through said hollow shaft.

5. The method of claim 1 wherein said cartridge includes an externally actuatable piston extending into said reservoir, and wherein said body fluid is expelled from said reservoir by forcing said piston into said reservoir.

6. The method of claim 5, wherein said body fluid is conveyed from said body fluid analyzer back to said sampling cartridge by drawing said piston out of said reservoir thereby creating a suction in said reservoir.

7. The method of claim 1, wherein said cartridge includes an evacuated container positioned within said cartridge, and wherein said body fluid is drawn from the patient into said reservoir by selectively coupling the vacuum in said evacuated container to the interior of said reservoir thereby drawing body fluid through the first port of said reservoir into said reservoir.

8. The method of claim 7, wherein said evacuated container is fabricated from a frangible material, and wherein said vacuum is selectively coupled to interior of said reservoir by fracturing said evacuated container.

9. The method of claim 7, wherein said cartridge includes a resilient seal covering the first port of said reservoir, a resilient tab positioned adjacent to said evacuated container, a tapered member coupled to said tab and extending radially beyond a sidewall of said cartridge, and a needle adapter having a cylindrical body portion, an end wall closing one end of said cylindrical body portion, and a double-ended needle projecting in opposite directions from said end wall along the axis of said body portion, the inside diameter of said body portion being just slightly larger than the outside diameter of said cartridge, and wherein said evacuated container is fractured by inserting said cartridge into said body portion until one end of said needle punctures the seal covering the first port of said reservoir and the cylindrical body portion inwardly displaces said tapered member thereby causing said tab to fracture said evacuated container.

10. The method of claim 1 wherein said body fluid reservoir is formed by an evacuated tube having an opening covered by a resilient septum, and wherein said body fluid is drawn into said evacuated tube by inserting a needle through said resilient septum into said evacuated tube so that the vacuum in said tube draws said body fluid into said tube.

11. The method of claim 10 wherein said evacuated tube further includes a breakaway piston slidably disposed therein, and wherein said body fluid is expelled from said tube by inserting an actuating member into said breakaway piston and forcing said actuating member against said piston thereby sliding said piston in said tube to expel said body fluid through an outlet port communicating with said body fluid analyzer.

12. The method of claim 11 wherein said actuating member is a hypodermic needle having a port opening into said waste collection chamber, and wherein, after said body fluid has been analyzed, said body fluid and said analyzing fluids are conveyed to said waste collection chamber by forcing said hypodermic needle through said breakaway piston thereby allowing fluid communication between said waste collection chamber and said outlet port, and then conveying said body fluid and analyzing fluid from said body fluid analyzer to said outlet port.

13. The method of claim 1 wherein a passage extends from said reservoir to said waste chamber, wherein a piston is placed is a first position to block said passage when said body fluid sample is taken from said patient, wherein said piston is placed in a second position to open said passage after the body fluid in said reservoir has been conveyed to said body fluid analyzer, and wherein said body fluid and analyzing fluids are conveyed from said body fluid analyzer to said waste collection chamber through said reservoir.

14. The method of claim 1 wherein said cartridge includes a housing having a front portion containing said reservoir and a rear portion containing said analyzing fluids, said front and rear portions being rotatably disposed with respect to each other, one of said portions having a cartridge outlet port adapted to communicate with said body fluid analyzer, and valve means includes a first opening in the rear face of said front portion radially spaced from the central axis of said cartridge, said first opening communicating with said outlet port, said valve means further including a plurality of second openings in the front face of said rear portion, said second openings being radially spaced from the central axis of said cartridge by the same distance that said first opening is spaced from the central axis of said cartridge and being circumferentially spaced apart from each other, each of said second openings communicating with the fluid port of a respective ampule, and wherein said analyzing fluids are successively conveyed from said body fluid collection cartridge to said outlet port by successively rotating said front portion with respect to said rear portion to a plurality of discrete angular orientations thereby successively aligning said first opening with respective second openings to allow respective ampules to communicate with said outlet port.

15. The method of claim 1 wherein said body fluid is expelled from said cartridge to said body fluid analyzer before said analyzing fluid is expelled from said cartridge to said body fluid analyzer.

16. The method of claim 1 wherein fluid is conveyed from said body fluid analyzer to said waste collection chamber after said body fluid and said analyzing fluid are expelled from said cartridge to said body fluid analyzer.

17. The method of claim 16 wherein the fluid conveyed from said body fluid analyzer to the waste collection chamber of cartridge is the body fluid sample and analyzing fluid that was previously expelled to said body fluid analyzer from that same cartridge so that the body fluid sample and analyzing fluid stored in a cartridge is returned to that cartridge after passing through said body fluid analyzer.

18. The method of claim 1 wherein said disposable sampling cartridge contains a plurality of analyzing fluids, and wherein said analyzing fuilds are successively expelled from said sample collection cartridge into said body fluid analyzer either before or after said body fluid has been expelled from said reservoir into said body fluid analyzer and before or after said fluid has been conveyed from said body fluid analyzer to said waste collection chamber.

19. A disposable sampling cartridge for use with a body fluid analyzer, comprising:
a reservoir having a first port adapted to receive a body fluid from a patient;
a waste collection chamber adapted to receive waste fluids from said body fluid analyzer;
a chamber containing an analyzing fluid adapted for use by said body fluid analyzer;
first means for expelling said body fluid from said reservoir into said body fluid analyzer;
second means for causing and analyzing fluid to flow from said chamber into said body fluid analyzer; and
third means for conveying fluids from said body fluid analyzer into said waste collection chamber.

20. The disposable sampling cartridge of claim 19 wherein said reservoir is vented through a second port which is blocked by an air-permeable, fluid-impermeable material so that body fluid flowing into said reservoir can displace air in said chamber through said material until said reservoir has been filled with said body fluid.

21. The disposable sampling cartridge of claim 20 wherein first and second passages extend between the second port of said reservoir and said waste chamber, and wherein said air-permeable, fluid-impermeable material is disposed in said first passage, said cartridge further including a piston selectively movable between first and second positions, said piston blocking said second passage in said first position thereby allowing said reservoir to vent into said waste chamber while preventing body fluid in said reservoir from flowing into said waste chamber, and said piston opening said second passage in said second position thereby allowing fluid in said reservoir to flow into said waste chamber.

22. The disposable sampling cartridge of claim 21 wherein said piston is movable into said reservoir toward the first port of said reservoir thereby forcing body fluid out of said reservoir through said first port when body fluid is to be analyzed.

23. The disposable sampling cartridge of claim 22 wherein the first port of said reservoir is accessible at one end of said cartridge, and wherein an aperture is formed in said cartridge at the other end of said cartridge in alignment with said piston so that said piston may be externally actuated through said aperture.

24. The disposable sampling cartridge of claim 23 further including a releasable clamp formed at the end of said piston closest to said aperture whereby said piston may be externally actuated to draw said piston out of said reservoir thereby suctioning fluid through said first port into said reservoir.

25. The disposable sampling cartridge of claim 19 further including a piston that is movable into said reservoir toward the first port of said reservoir thereby forcing body fluid out of said reservoir through said first port when said body fluid is to be analyzed.

26. The disposable sampling cartridge of claim 21 wherein the first port of said reservoir is accessible at one end of said cartridge, and wherein an aperture is formed in said cartridge at the other end of said cartridge in alignment with said piston so that said piston may be externally actuated through said aperture.

27. The disposable sampling cartridge of claim 26 wherein said chamber is formed by an ampule that is accessible at the end of said cartridge containing said aperture.

28. The disposable sampling cartridge of claim 27 wherein at least a portion of the wall of said ampule facing said the end of said cartridge containing said aperture is formed of a frangible material so that the analyzing fluid in said ampule may be accessed by puncturing said ampule from the same end of said cartridge through which said piston is actuated.

29. The disposable sampling cartridge of claim 26 wherein said piston extends along the longitudinal axis of said cartridge, and wherein said cartridge includes a plurality of said ampules circumferentially spaced around said piston.

30. The disposable sampling cartridge of claim 19 further including an evacuated container positioned wiithin said cartridge, said cartridge further including means for selectively coupling the vacuum in said evacuated container to the interior of said reservoir thereby drawing body fluid through the first port of said reservoir into said reservoir whereby said cartridge may be used for collecting venous body fluid.

31. The disposable sampling cartridge of claim 30 wherein said evacuated container is fabricated from a frangible material, and wherein said means for selectively coupling the vacuum in said evacuated container to the interior of said reservoir includes fracturing means for breaking said evacuated container.

32. The disposable sampling cartridge of claim 31 wherein said fracturing means includes a resilient tab positioned adjacent to said evacuated container, said tab being externally accessible so that it may be forced through a wall of said evacuated container to couple the vacuum in said evacuated container to said reservoir.

33. The disposable sampling cartridge of claim 32 further including a resilient seal covering the first port of said reservoir, and a tapered member coupled to said tab and extending radially beyond a sidewall of said cartridge, and wherein said cartridge further includes a needle adapter having a cylindrical body portion, an end wall closing one end of said cylindrical body portion, and a double-ended needle projecting in opposite directions from said end wall along the axis of said body portion, the inside diameter of said body portion being just slightly larger than the outside diameter of said cartridge so that inserting said cartridge into said body portion causes one end of said needle to puncture the seal covering the first port of said reservoir and the cylindrical body portion to inwardly displace said tapered member thereby causing said tab to fracture said evacuated container.

34. The disposable sampling cartridge of claim 19 wherein said reservoir is formed by an evacuated tube having an opening covered by a resilient septum so that said body fluid may be drawn into said evacuated tube by inserting a needle communicating with said body fluid through said resilient septum and into said evacuated tube.

35. The disposable sampling cartridge of claim 34 wherein said first means for expelling said body fluid includes a breakaway piston slidably disposed in said evacuated tube, and an actuating member adapted to force said breakaway piston against said piston thereby sliding said piston in said tube to expel said body fluid through an outlet port communicating with said body fluid analyzer.

36. The disposable sampling cartridge of claim 35 wherein said actuating member includes a hypodermic needle having a port opening into said waste collection chamber so that, after said body fluid has been analyzed, said body fluid and said analyzing fluids may be conveyed to said waste collection chamber by forcing said hypodermic needle through said breakaway piston thereby allowing fluid communication between said waste collection chamber and said outlet port.

37. The disposable sampling cartridge of claim 19 wherein said cartridge includes a housing having a front portion and a rear portion rotatably disposed with respect to each other, one of said portions having a cartridge outlet port adapted to communicate with said body fluid analyzer, said front portion containing said reservoir, and said rear portion including connecting means for connecting said reservoir and said outlet port when said front portion is rotated with respect to said rear portion to a first predetermined angular orientation.

38. The disposable sampling cartridge of claim 37 wherein said front portion further includes a vent line for venting air from said reservoir when body fluid flows into said reservoir through said first port, and wherein said connecting means connects said reservoir to said vent line when said front portion is rotated with respect to said rear portion to a second predetermined angular orientation.

39. The disposable sampling cartridge of claim 37 wherein said waste collection chamber is disposed in said front portion, and wherein said front portion further includes a cartridge inlet port communicating with said waste collection chamber for receiving said waste fluids from said body fluid analyzer.

40. The disposable sampling cartridge of claim 19 wherein said first means for expelling said body fluid from said reservoir includes a piston slidably disposed in said reservoir for pumping said body fluid therefrom.

41. The disposable sampling cartridge of claim 19 wherein said second means for causing said analyzing fluid to flow from said ampule includes an externally actuatable piston disposed in said ampule.

42. The disposable sampling cartridge of claim 41 wherein said actuatable piston includes a piston member slidably disposed in said ampule and a frangible wall in the rear face of said ampule for allowing said piston member to be actuated through the rear face of said ampule.

43. The disposable sampling cartridge of claim 41 wherein said ampule includes a fluid port, and wherein said cartridge includes valve means for coupling each of the fluid port of said ampule to said outlet port depending on the angular position of said rear portion with respect to said front portion.

44. The disposable sampling cartridge of claim 41 wherein said valve means includes a first opening in the rear face of said front portion radially spaced from the central axis of said cartridge, said first opening communicating with said outlet port, said valve means further including a plurality of second openings in the front face of said rear portion, said second openings being radially spaced from the central axis of said cartridge by the same distance that said first opening is spaced from the central axis of said cartridge and being circumferentially spaced apart from each other, each of said second openings communicating with the fluid port of a respective ampule so that rotation of said front portion with respect to said rear portion to a plurality of discrete angular orientations aligns said first opening with respective second openings thereby allowing respective ampules to communicate with said outlet port.

45. The disposable sampling cartridge of claim 19 wherein said cartridge includes a plurality of chambers each containing a respective analyzing fluid, and wherein said second means causes said analyzing fluids to flow in sequence from said chambers to said body fluid analyzer.

46. The disposable sampling cartridge of claim 19 wherein said second means causes said analyzing fluid to flow from said chamber to said body fluid analyzer by forcibly expelling said analyzing fluid from said chamber.

47. The disposable sampling cartridge of claim 46 wherein the fluid conveyed from said body fluid analyzer to the waste collection chamber of a cartridge is the body fluid and analyzing fluid that was previously conveyed to said body fluid analyzer from that same cartridge so that the body fluid and analyzing fluid stored in a cartridge is returned to that cartridge after passing through said body fluid analyzer.

48. The disposable sampling cartridge of claim 19 wherein said third means conveys fluid from said body fluid analyzer to said waste collection chamber after said first means has expelled said body fluid from said reservoir to said body fluid analyzer the fluids and said second means has been caused to flow from said chamber to said body fluid analyzer.

49. A device for sampling a body fluid, comprising:
a housing;
body fluid withdrawing means for withdrawing body fluid from a patient into said housing;
body fluid transfer means for transferring said body fluid from said housing to an exterior body fluid analyzer;
storing means for storing an analyzing fluid in said housing; and
fluid transfer means for transferring said analyzing fluid from said housing into said body fluid analyzer to flush said body fluid therefrom.

50. The device of claim 49 wherein said storing means comprises an ampule disposed in said housing.

51. The device of claim 49, further comprising a waste chamber disposed in said housing for storing said body fluid and said analyzing fluid after said body fluid and said analyzing fluid have passed through said analyzer.

* * * * *

UNITED STATES PATENT AND TRADEMARK OFFICE
CERTIFICATE OF CORRECTION

PATENT NO. : 5,143,084
DATED : September 1, 1992
INVENTOR(S) : James H. Macemon; Mark S. Schlosser It is certified that error appears in the above-identified patent and that said Letters Patent is hereby corrected as shown below:

In column 16, claim 18, line 64, please delete "fuilds" and substitute therefor -- fluids --.

In column 17, claim 26, line 61, please delete "claim 21" and substitute -- claim 25 --.

Signed and Sealed this

Twenty-first Day of September, 1993

Attest:

BRUCE LEHMAN

Attesting Officer

Commissioner of Patents and Trademarks